(12) United States Patent
Ukai et al.

(10) Patent No.: US 7,727,552 B1
(45) Date of Patent: Jun. 1, 2010

(54) ORAL PHARMACEUTICAL PREPARATIONS DECREASED IN BITTERNESS BY MASKING

(75) Inventors: Koji Ukai, Gifu (JP); Tsutomu Hrada, Aichi (JP); Yasuyuki Suzuki, Gifu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 09/380,310

(22) PCT Filed: Mar. 26, 1998

(86) PCT No.: PCT/JP98/01360

§ 371 (c)(1),
(2), (4) Date: Aug. 31, 1999

(87) PCT Pub. No.: WO98/43675

PCT Pub. Date: Oct. 8, 1998

(30) Foreign Application Priority Data

Mar. 28, 1997 (JP) .................................. 9-078568
Dec. 12, 1997 (JP) .................................. 9-343265

(51) Int. Cl.
*A61K 9/20* (2006.01)
*A61K 9/34* (2006.01)
*A61K 9/68* (2006.01)
*A61K 47/32* (2006.01)

(52) U.S. Cl. ...................... 424/489; 424/488; 424/485; 424/465; 424/479; 424/441; 424/481; 514/772.4; 514/974

(58) Field of Classification Search ................. 424/452, 424/70.11, 481, 78.1, 246, 440, 441, 489, 424/488, 485, 465, 479; 514/772.4, 974
See application file for complete search history.

(56) References Cited

U.S. PATENT DOCUMENTS

| | | | |
|---|---|---|---|
| 4,313,529 A * | 2/1982 | Kato et al. | |
| 4,725,440 A | 2/1988 | Ridgway et al. | |
| 5,013,557 A | 5/1991 | Tai | |
| 5,077,053 A | 12/1991 | Kuncewitch et al. | |
| 5,084,278 A | 1/1992 | Mehta | |
| 5,286,489 A | 2/1994 | Tsau et al. | |
| 5,288,501 A | 2/1994 | Nurnberg et al. | |
| 5,464,612 A * | 11/1995 | Matoba et al. .............. | 424/78.1 |
| 5,466,464 A | 11/1995 | Masaki et al. | |
| 5,489,436 A | 2/1996 | Hoy et al. | |
| 5,576,014 A | 11/1996 | Mizumoto et al. | |
| 5,612,026 A * | 3/1997 | Diehl ...................... | 424/78.01 |
| 5,656,284 A * | 8/1997 | Balkin et al. ................ | 424/435 |
| 5,763,449 A | 6/1998 | Anaebonam et al. | |
| 5,827,507 A | 10/1998 | Oshima et al. | |
| 5,874,074 A | 2/1999 | Smith | |
| 5,955,106 A | 9/1999 | Moeckel et al. | |
| 5,962,535 A | 10/1999 | Miyamoto et al. | |
| 6,214,386 B1 | 4/2001 | Santus et al. | |
| 6,368,625 B1 | 4/2002 | Siebert et al. | |
| 6,455,053 B1 | 9/2002 | Okada et al. | |
| 6,576,677 B1 | 6/2003 | Ukai et al. | |
| 6,586,004 B2 | 7/2003 | Shimizu et al. | |
| 6,656,492 B2 | 12/2003 | Kajiyama et al. | |
| 6,743,443 B1 | 6/2004 | Furitsu et al. | |

FOREIGN PATENT DOCUMENTS

| | | |
|---|---|---|
| EP | 0 590 963 A1 | 4/1994 |
| EP | 0 691 122 A2 | 1/1996 |
| EP | 0 748 628 A2 | 12/1996 |
| EP | 0 753 296 A2 | 1/1997 |
| EP | 0 922 464 A1 | 6/1999 |
| EP | 1 120 120 A1 | 8/2000 |
| JP | 51-76413 | 7/1976 |
| JP | 5476818 | 6/1979 |
| JP | 60-204712 A | 10/1985 |
| JP | 61-130239 A | 6/1986 |
| JP | 03-005418 A | 1/1991 |
| JP | 4282312 A | 10/1991 |
| JP | 03-287535 A | 12/1991 |
| JP | 04-018015 A | 1/1992 |
| JP | 4-235136 A | 8/1992 |
| JP | 4-235136 A | 8/1992 |
| JP | 4-262758 A | 8/1992 |
| JP | 4-346937 A | 12/1992 |
| JP | 4346937 | 12/1992 |
| JP | 5-163154 A | 8/1993 |
| JP | 5-271054 A | 10/1993 |
| JP | 6-218028 A | 8/1994 |

(Continued)

OTHER PUBLICATIONS

Drug Information on Vantin® by Pharmacia /& upjohn, obtained through on-line PDR (revised Nov. 2000).*

(Continued)

*Primary Examiner*—Mina Haghighatian
(74) *Attorney, Agent, or Firm*—Birch, Stewart, Kolasch & Birch, LLP

(57) ABSTRACT

A composition of an oral medicine or an oral medicine which can prevent an unpleasant taste of the medicine is herein disclosed. It is granules, powders, syrups and the like which is prevented from an unpleasant taste, comprising a basic medicine having an unpleasant taste and an anionic polymer such as carrageenan.

6 Claims, No Drawings

FOREIGN PATENT DOCUMENTS

| | | |
|---|---|---|
| JP | 07267850 A | 10/1995 |
| JP | 8-19589 A | 1/1996 |
| JP | 8-333245 A | 12/1996 |
| JP | 9-48726 A | 2/1997 |
| JP | 09-143100 A | 6/1997 |
| JP | 10-0036292 A | 2/1998 |
| JP | 10-114683 A | 5/1998 |
| JP | 2807346 B2 | 7/1998 |
| JP | 41-1106353 | 4/1999 |
| JP | 11-199517 A | 7/1999 |
| JP | 11-228450 A | 8/1999 |
| JP | 2005-041887 | 2/2005 |
| WO | WO 99/18936 A1 | 4/1999 |
| WO | WO-00/20033 A1 | 4/2000 |
| WO | WO-00/25754 A2 | 5/2000 |

OTHER PUBLICATIONS

Research Disclosure 176019 (Derwent WPI Acc No. 78-92367 A/51) (1978).*

Drug Information for Vantin, Physicain's Desk Reference- 1995.*

Kawakami, Y.; Inoue, A.; Kawai, T.; Wakita, M.; Sugimoto, H. Hopfinger, A. J. Bioorganic & Med, Chem. Lett. 1996, 4, (1429-1446).*

1998 Physician Desk Reference, p. 1203.

Wade and Weller-Editors: Handbook of Pharmaceutical Excipients, Povidone, p. 392, 1994.

Supplementary Search Report issued on Jan. 27, 2006, in connection with European Patent Application No. 01 908 204.9-2123.

Official European Patent Office Communication dated Sep. 13, 2006, issued in connection with European Patent Application No. 01 908 402.9-2123.

Applicant's Response dated Mar. 19, 2007, in response to Official Communication issued on Sep. 13, 2006, in connection with European Patent Application No. 01 908 204.9-2123.

Official European Patent Office Communication dated Oct. 17, 2008, issued in connection with European Patent Application No. 01 908 204.9-2123.

Applicant's Response dated Jan. 23, 2009, in response to Official Communication issued on Oct. 17, 2008, in connection with European Patent Application No. 01 908 204.9-2123.

Notice of Acceptance issued Feb. 20, 2009, in connection with European Patent Application No. 01 908 204.9-2123.

U.S. Appl. No. 10/203,687 dated Oct. 20, 2004.
U.S. Appl. No. 10/203,687 dated Jul. 13, 2005.
U.S. Appl. No. 10/203,687 dated Mar. 06, 2006.
U.S. Appl. No. 10/203,687 dated Jan. 16, 2007.
U.S. Appl. No. 10/203,687 dated Nov. 30, 2007.
U.S. Appl. No. 10/203,687 dated Aug. 15, 2008.

* cited by examiner

ORAL PHARMACEUTICAL PREPARATIONS DECREASED IN BITTERNESS BY MASKING

Oral medicine preventing unpleasant taste and the like. This application is the national phase under 35 U.S.C. § 371 of PCT International Application No. PCT/JP98/01360 which has an International filing date of Mar. 26, 1998, which designated the United States of America.

FIELD OF THE INVENTION

The present invention relates to an oral administration composition or an oral medicine which can prevent an unpleasant taste.

PRIOR ART

For masking a medicine having an unpleasant taste, a lot of techniques have been developed. For example, there is known a method for coating a granulated agent with a water-soluble film (JP-A 4-282312), and a method for obtaining a powder and the like by melting a waxy substance having a melting point in the range of 40 to 100° C. wherein a medicine having an unpleasant taste is allowed to be dispersed and then solidified (JP-A 7-267850). On the other hand, for liquids, in order to improve the feeling of taking medicine, there is known a method to use liquids on oral administration such as syrups, which is widely used as a dosage form suitable for infants, aged people, etc. Although syrup is a dosage form with a sweet taste, when a melted medicine has an unpleasant taste, it is difficult to administer it, because a mere sweet taste cannot prevent an unpleasant taste, and in addition, compliance of a patient is lowered. Moreover, in JP-A 4-346937, as a method for reducing a bitter taste, there has been disclosed a method for reducing a bitter taste which comprises the step of adding a gelling agent selected from agar, gelatin or κ-carrageenan, and a seasoning agent to a substance having a bitter taste, so that a jelly state for seasoning is obtained. This method reduces a contact of a bitter taste substance with a tongue by making a jelly state, and a partly melted bitter taste substance masks a bitter taste by the use a seasoning agent.

With a view to masking a medicine having an unpleasant taste, a lot of techniques have been examined as described above, but they have a complicated manufacturing process, an inadequate effect and a problem in quality. Thus, they have not yet been satisfactory, so that a further technique is required.

DISCLOSURE OF THE INVENTION

The present invention is directed to an oral medicine composition or an oral medicine preventing an unpleasant taste, which comprises a basic medicine having the unpleasant taste and an anionic polymer, or a method for preventing the same.

A basic substance referred to in the present invention means that its free form shows basicity, and in case of the formation of a salt form, it is not necessarily basic.

In the present invention, a basic medicine having an unpleasant taste should not be limited, therefore, among orally administrated medicines such as an antibiotic substance, an antidementia medicine, an antiplatelet medicine, an antidepressive medicine, a medicine for improving metabolism of a brain circulation, or an antiallergic medicine, a basic medicine having an unpleasant taste such as a stimulation can be used. Embodied examples of the basic substance include ticlopidine hydrochloride, maprotiline hydrochloride, ifenprodil tartrate, berberine hydrochloride, digitoxin, sulpyrin, azelastine hydrochloride, etilefrin hydrochloride, diltiazem hydrochloride, propranolol hydrochloride, chloramphenicol, aminophylline, erythromycin, phenobarbital, calcium pantothenic acid, indeloxazine hydrochloride, aminoguanidine hydrochloride, donepezil hydrochloride, (RS)-1-(isopropoxycarbonyloxy)ethyl(+)-(6R,7R)-7{(z)-2-(2-aminothiazole-4-yl)-2-hydroxyiminoacetamide}-3-N,N-dimethylcarbamoyloxymethyl-8-oxo-5-thia-1-azabicyclo[4.2.0]octo-2-en-2-carboxylate hydrochloride salt, cefcapene pivoxil hydrochloride and the like. Among these compounds, for donepezil hydrochloride and (RS)-1-(isopropoxycarbonyloxy)ethyl(+)-(6R,7R)-7{(z)-2-(2-aminothiazole-4-yl)-2-hydroxyiminoacetamide}-3-N,N-dimethylcarbamoyloxymethyl-8-oxo-5-thia-1-azabicyclo[4.2.0]octo-2-en-2-carboxylate hydrochloride salt, an especially excellent effect is exerted. Donepezil hydrochloride is chemically named (1-benzyl-4-(5,6-dimethoxyindanon-2-yl)methylpiperidine hydrochloride salt, which is therapeutic medicine for Alzheimer's disease to a slight to a medium degree, and its aqueous solution has a sharp bitterness and a numbness in a mouth. In addition, (RS)-1-(isopropoxycarbonyloxy)ethyl (+)-(6R,7R)-7{(z)-2-(2-aminothiazole-4-yl)-2-hydroxyiminoacetamide}-3-N,N-dimethylcarbamoyloxymethyl-8-oxo-5-thia-1-azabicyclo[4.2.0]octo-2-en-2-carboxylate hydrochloride is an effective antibiotics on oral administration, however, it has a strong bitter taste.

Although an anionic polymer referred to in the present invention should not especially be limited, an acidic polysaccharide is preferable, and typical examples include carrageenan, chondroitin sulfate, dextran sulfate, alginic acid, gerun gum, xanthan gum and a salt form thereof. With regard to carrageenan, some kinds such as ι, κ, λ and the like are known, and any kind can be used, and especially, for liquids or jellies, κ-carrageenan and λ-carrageenan are preferable, and dextran sulfate is also preferable.

For solids, especially κ-carrageenan, chondroitin sodium sulfate and sodium alginate are preferable.

Carrageenan on the market can be used, and it is obtainable from FMC Corporation: USA, Systems Bio Industries Co., Ltd. etc.

An oral medicine regarding the present invention means a dosage form which can be orally administrated as solids, liquids or jellies. Typical examples of the solids include granules, fine granules, powders, tablets, pills etc., and typical examples of the liquids include syrups, elixirs, emulsions, suspensions and the like, and especially, a case of granules, fine granules, powders, syrups and jellies are preferable.

These dosage forms are described in the Japanese Pharmacopoeia except for jellies.

A method for administration of an oral medicine related to the present invention should not be especially limited, and according to a property of a medicine, the oral medicine can be orally administrated one to several times per day before, after or between meals.

Since the amount of a medicine in solids is different according to a property of a medicine, it is not generally spoken, but the amount of the medicine at one administration is usually in the range of 0.1 to 1000 mg.

The concentration of a medicine in oral liquids which prevents an unpleasant taste is usually in the range of 0.1 to 500 mg/ml, preferably in the range of 0.5 to 100 mg/ml. When a medicine is donepezil hydrochloride, the concentration is preferably in the range of 0.5 to 5 mg/ml.

In the present invention, the proportion of an anionic polymer to a basic substance is usually in the range of 0.1 to 20 parts by weight, preferably 0.5 to 10 parts by weight with respect to 1 part by weight of a basic substance.

In the case that the oral medicine regarding the present invention is the solids, the medicine and the anionic polymer are homogeneously mixed to obtain an effect of preventing an unpleasant taste. Furthermore, the medicine and fillers and the like are mixed, and separately, an anionic polymer is dissolved in a solvent such as water, mixed with another binding agent, if necessary, and then gradually added to the medicine to be granulated, as a result, an effect of preventing an unpleasant taste is also obtainable. Depending upon a kind of a medicine, some medicines have greater effect preventing an unpleasant taste by being granulated.

A method for manufacturing an oral medicine preventing an unpleasant taste related to the present invention should not be especially limited, and the medicine can be manufactured by a method which is usually used. For example, for a granule medicine, an excipient such as milk sugar, manitol, a starch and crystal cellulose, a disintegrating agent and the like, such as carboxymethycellulose, are mixed into a medicine and κ-carrageenan, with adding a solution wherein a binding agent such as hydroxypropylcellulose, the granule medicine can be manufactured by the use of a granulater which is usually used. In addition, a method for manufacturing an oral liquid medicine should not be especially limited. For example, a basic medicine and an anionic polymeric substance are dissolved in water to manufacture the oral liquid medicine. Furthermore, a sweetening agent such as cane sugar, xylitol, mannitol, glucose, aspartame and saccharin, and a taste-reforming agent such as vanilla essence and apple odor can be added to it. Since the oral medicine related to the present invention prevents an unpleasant taste such as a bitter taste, numbness and contraction, it is easily administrated and compliance of a patient improves. Especially, the present invention is effective on infants, aged people. A mechanism that the oral medicine related to the present invention prevents an unpleasant taste is considered as follows. That is to say, it is considered that when a basic substance having an unpleasant taste brings about an interaction with an acidic polysaccharide to be dissolved in saliva, or through decrease of liberated bodies in a solution, a bonding rate of the basic substance to a receptor of a tongue is decreased, and in addition, appearance of numbness is also decreased.

Experimental Example

Test 1

2 mg/ml of an aqueous donepezil hydrochloride solution was prepared. After 50 mg of κ-carrageenan, chondroitin sulfate or dextran sulfate was dissolved in 5 ml of the aqueous solution. Afterward, two examinees (which were represented by A and B in Table 1) hold the whole amount of the solution in their mouths, and then evaluated the degree of a bitter taste and numbness in accordance with five grades. The results are shown in Table 1.

As is apparent from Table 1, a bitter taste of donepezil hydrochloride can be remarkably controlled by the addition of λ-carrageenan and the like.

Test 2

By the use of ticlopidine hydrochloride (20 mg/ml), maprotiline hydrochloride (5 mg/ml) and iphenprodil tartaric acid (4 mg/ml), an effect of carrageenan preventing a bitter taste and numbness was examined. A method of examination and a standard of evaluation were based on Test 1. The results are shown in Table 2.

As is apparent from Table 2, a bitter taste and numbness of each medicine can be remarkably controlled by the addition of carrageenan. Especially, a taste of ticlopidine hydrochloride is extremely bitter and stimulative, but it proves the extremely excellent effect of the present invention that the bitter taste and numbness can be remarkably controlled by addition of carrageenan.

Test 3

Sodium alginate, sodium chondroitin sulfate, K carrageenan, 1-carrageenan, mannitol, cornstarch, copolyvidon and the like were blended with (RS)-1-(isopropoxycarbonyloxy) ethyl(+)-(6R,7R)-7{(z)-2-(2-aminothiazole-4-yl)-2-hydroxyiminoacetamide}-3-N,N-dimethylcarbamoyloxymethyl-8-oxo-5-thia-1-azabicyclo-[4.2.0]octo-2-en-2-carboxylate hydrochloride salt (which was shown as a compound A in Table 3) in ratios shown in Table 2, and granules were prepared in accordance with the method of Example 3. The test was carried out by three examinees holding 0.5 g of each granule for examination in their mouths, and the judgment was done by an evaluation standard of seven grades shown as follows.

+4: impossible to administrate because of a severe bitterness, +3: very bitter, +2: bitter, +1: a little bitter, 0: neither taste, −1: feeling no bitterness, −2: rather delicious The results are shown in Table 3.

It is apparent from Table 3 that the granules combined with the anionic polymer related to the present invention remarkably controls a bitter taste.

Test 4

According to the treatment shown in Table 4, ticlopidine hydrochloride, κ-carrageenan, cornstarch, mannitol and hydroxypropylcellulose (which was represented by HPC-L in Table 4) were sufficiently mixed and water was then added, and they were granulated to obtain granules. Two examinees held 0.5 g of this granules in their mouths, and the judgment was done. The evaluation standard was based on Example 1. The result was shown in Table 4.

It is apparent from Table 4 that the present applied invention can prevent an extremely unpleasant taste of ticlopidine even in the solid state.

From the tests shown above, the remarkable effect of the present applied invention is evident.

EXAMPLES

Next, the present invention will be described in more detail in accordance with examples, but the scope of the present invention should not be limited by these examples.

Example 1

100 mg of donepezil hydrochloride, 300 mg of sodium saccharin and 14 g of povidone were dissolved in 50 g of purified water, and separately, 700 mg of κ-carrageenan was added to 50 g of purified water, and it was were heated at 80° C. to be dissolved. After it was cooled down, both solutions were mixed, and 300 mg of methylparabene and 20 mg of propylparabene were dissolved in a small quantity of propyleneglycol to be added to the above mixture, so that syrups were manufactured.

Example 2

40 g of xylitol was added to 50 g of purified water, and they were heated at 80° C. to be dissolved. And separately, 200 mg of donepezil hydrochloride was dissolved in 50 ml of purified water, and wherein 0.56 g of κ-carrageenan, 1.0 g of λ-carrageenan, 0.15 g of locust bean gum, 0.22 g of gerun gum, 0.15 g of xanthan gum, 0.19 g of sodium citrate, 0.19 g of calcium lactate, 0.94 g of lactose and 40 g of powdered hydrogenated maltose starch syrup were added, and in addition, the previously prepared xylitol-containing purified water was added therein, and they were stirred at 90° C. After the mixture was cooled down to 80° C., 0.6 g of citric acid was mixed therein, to which purified water was added, so that the total weight was 200 g. It was pipetted into vessels in a portion of 10 g and then cooled down to manufacture jellies.

Example 3

15 g of (RS)-1-(isopropoxycarbonyloxy)ethyl(+)-(6R, 7R)-7{(z)-2-(2-aminothiazole-4-yl)-2-hydroxyiminoacetamide}-3-N,N-dimethylcarbamoyloxymethyl-8-oxo-5-thia-1-azabicyclo[4.2.0]octo-2-en-2-carboxylate hydrochloride salt, g of κ-carrageenan, 30 g of cornstarch and 40 g of mannitol were mixed by the use of the rolling granuator, and about 20 ml of water was slowly added therein and wet mass was manufactured, and then dried through a screen with 32 meshes, so that granules were manufactured.

Example 4

15 g of the drug substance medicine used in Example 3, 15 g of sodium condroitin sulfate and 70 g of mannitol were mixed by the use of the granulator, and about 20 ml of water was slowly added therein and wet mass was manufactured, and then dried through a screen with 32 meshes, so that granules were manufactured.

Example 5

15 g of the drug substance used in Example 3, 15 g of carrageenan (mixture of ι-carrageenan and κ-carrageenan), 15 g of copolyvidon and 55 g of mannitol were mixed by the use of the granulator, and about 15 ml of water was slowly added therein and wet mass was manufactured, and then dried through a screen with 32 meshes, so that granules were manufactured.

Example 6

58 g of the drug substance used in Example 3, 58 g of κ-carrageenan, 120 g of cornstarch, 130 g of mannitol and 16 g of aerosil were mixed, whereon 8 g of sodium alginate dissolved in 392 ml of water and a slight amount of Red-102 pigment were sprayed by the use of the fluidized bed granulator, and then they were dried. Next, 2 g of strawberry essence was sprayed thereon and they were dried, wherein 8 g of aspartame was mixed, so that fine granules were manufactured.

Example 7

15 g of the drug substance used in Example 3, 14.5 g of κ-carrageenan, 30 g of cornstarch and 40 g of mannitol were mixed, whereon 0.5 g of λ-carrageenan dissolved in 25 ml of water was sprayed by the use of the fluidized bed granulator, so that fine granules were manufactured.

Example 8

10 g of cefcapene pivoxil hydrochloride, 10 g of κ-carrageenan, 30 g of cornstarch, 48 g of mannitol and 2 g of aspartame were mixed by the use of a rolling granulator, and 20 ml of water was slowly added thereto and wet mass was manufactured, and then dried through a screen with 32 meshes, so that granules were manufactured.

TABLE 1

| Standard of Evaluation | | | | | |
| --- | --- | --- | --- | --- | --- |
| Bitterness | No Feeling | Dim Feeling | Slightly bitter | Bitter | Very bitter |
| Numbness | No Feeling | Dim Feeling | Slightly numb | Numb | Very numb |
| | − | ± | + | ++ | +++ |

Results

| | A | | B | |
| --- | --- | --- | --- | --- |
| Sample/Examinee | Bitterness | Numbness | Bitterness | Numbness |
| Donepezil hdyrochloride | +++ | +++ | +++ | +++ |
| Donepezil hydrochloride + κ-Carrageenan | + | ± | + | + |
| Donepezil hydrochloride + Condroitin sulfate | ++ | ++ | +++ | ++ |
| Donepezil hydrochloride + Dextran sulfate | + | ± | + | + |

TABLE 2

| | A | | B | |
| --- | --- | --- | --- | --- |
| Sample/Examinee | Bitterness | Numbness | Bitterness | Numbness |
| Ticlopidine sulfate | +++ | +++ | +++ | +++ |
| Ticlopidine sulfate + κ-Carrageenan (1 mg/ml) + λ-Carrageenan (1 mg/ml) | ± | ++ | ± | ++ |
| Ticlopidine sulfate + κ-Carrageenan (2 mg/ml) | − | + | − | ± |
| Maprotiline hydrochloride | ++ | + | + | + |
| Maprotiline hydrochloride + κ-Carrageenan (2 mg/ml) | − | − | − | − |
| Iphenprodil tartaric acid | + | − | ++ | − |
| Iphenprodil tartaric acid + κ-Carrageenan (2 mg/ml) | ± | − | − | − |

TABLE 3

| Composition | Prescription (%) | Evaluater A | Evaluater B | Evaluater C |
| --- | --- | --- | --- | --- |
| Compound A | 15 | +4 | +3 | +4 |
| Mannitol | 85 | | | |
| Compound A | 15 | +1 | 0 to +2 Note 1 | +1 |
| Sodium alginate | 15 | | | |
| Mannitol | 70 | | | |
| Compound A | 15 | 0 | 0 | 0 |
| Sodium condroitin sulfate | 15 | | | |
| Mannitol | 70 | | | |
| Compound A | 15 | 0 | 0 | 0 |
| κ-Carrageenan | 15 | | | |
| Cornstarch | 30 | | | |

TABLE 3-continued

| Composition | Prescription (%) | Evaluater A | Evaluater B | Evaluater C |
|---|---|---|---|---|
| Mannitol | 40 | | | |
| Compound A | 15 | −1 | 0 to +1 | 0 |
| κ & ι-Carrageenan | 15 | | Note 1 | |
| Copolyvidon | 15 | | | |
| Mannitol | 55 | | | |
| Compound A | 15 | 0 | −1 | 0 |
| κ-Carrageenan | 14.5 | | | |
| λ-Carrageenan | 0.5 | | | |
| (solvent was added) | | | | |
| Cornstarch | 30 | | | |
| Mannitol | 40 | | | |
| Compound A | 14.5 | −2 | −2 | −2 |
| κ-Carrageenan | 14.5 | | | |
| sodium alginate | 2 | | | |
| (solvent was added) | | | | |
| Cornstarch | 30 | | | |
| Mannitol | 32.5 | | | |
| Aerosil | 4 | | | |
| Strawberry essence | 0.5 | | | |
| Red No. 102 | Trace | | | |
| Aspartame | 2 | | | |

Note 1: When it was administered with water, the bitterness was felt afterward.

Note 1: When it was administered with water, the bitterness was felt afterward.

TABLE 4

| | | Control | Prescription 1 | Prescription 2 | Prescription 3 |
|---|---|---|---|---|---|
| Prescription | Ticlopidine | 100 | 100 | 100 | 100 |
| | κ-Carrageenan | 0 | 100 | 200 | 300 |
| | Mannitol | 670 | 570 | 470 | 370 |
| | Cornstarch | 200 | 200 | 200 | 200 |
| | HPC-L | 30 | 30 | 30 | 30 |
| | Total | 1000 | 1000 | 1000 | 1000 |
| Results | A Bitterness | + | ± | − | − |
| | Numbness | +++ | +++ | + | ± |
| | B Bitterness | + | + | − | − |
| | Numbness | +++ | +++ | ± | − | mg/g of a granule

The invention claimed is:

1. An oral medicine preventing an unpleasant taste which comprises a mixture comprising a basic medicine having an unpleasant taste and an acidic polysaccharide, wherein
the mixture is in a homogeneous blend and said basic medicine and acidic polysaccharide are in intimate contact in order to form an electric interaction and to prevent the basic medicine from dissolving in saliva;
said homogeneous blend further comprises a filler, a binding agent or disintegrant, or both a filler and a disintegrant;
said medicine is in the form of granules or fine granules for oral administration or a tablet for oral administration comprising the homogeneous blend;
said acidic polysaccharide is at least one member selected from the group consisting of carrageenan and salts thereof;
said acidic polysaccharide is in an amount of 0.1 to 20 parts by weight with respect to 1 part by weight of the basic substance having the unpleasant taste, and
said basic medicine is donepezil hydrochloride.

2. A method for manufacturing an oral medicine in the form of granules or fine granules for oral administration or a tablet for oral administration, said medicine comprising a mixture comprising basic medicine having an unpleasant taste and an acidic polysaccharide, said method comprising:
blending the mixture to obtain a homogeneous blend of said oral medicine; wherein said acidic polysaccharide is in an amount of 0.1 to 20 parts by weight with respect to 1 part by weight of the basic medicine; and
forming the mixture comprising the homogeneous blend into granules, fine granules or a tablet for oral administration,
wherein said basic medicine and acidic polysaccharide are in intimate contact in order to form an electric interaction and to prevent the basic medicine from dissolving in saliva; wherein said homogeneous blend further comprises a filler, a disintegrant, or both a filler and a disintegrant to obtain said homogeneous blend; wherein said acidic polysaccharide is at least one member selected from the group consisting of carrageenan and salts thereof; and wherein said basic medicine is donepezil hydrochloride.

3. The oral medicine of claim 1, wherein the carrageenan is at least one member selected from the group consisting of ι-carrageenan, κ-carrageenan, λ-carrageenan, and a salt thereof.

4. The method of claim 2, wherein the carrageenan is at least one member selected from the group consisting of ι-carrageenan, κ-carrageenan, λ-carrageenan, and a salt thereof.

5. An oral medicine preventing an unpleasant taste which comprises a mixture comprising a basic medicine having an unpleasant taste and an acidic polysaccharide, wherein
the mixture is in a homogeneous blend and said basic medicine and acidic polysaccharide are in intimate contact in order to form an electric interaction and to prevent the basic medicine from dissolving in saliva;
said homogeneous blend further comprises a filler, a binding agent or disintegrant, or both a filler and a disintegrant;
said medicine is in the form of granules or fine granules for oral administration or a tablet for oral administration comprising the homogeneous blend;
said acidic polysaccharide is at least one member selected from the group consisting of chondroitin sulfate, dextran sulfate, and salts thereof;
said acidic polysaccharide is in an amount of 0.1 to 20 parts by weight with respect to 1 part by weight of the basic substance having the unpleasant taste, and
said basic medicine is donepezil hydrochloride.

6. A method for manufacturing an oral medicine in the form of granules or fine granules for oral administration or a tablet for oral administration, said medicine comprising a mixture comprising basic medicine having an unpleasant taste and an acidic polysaccharide, said method comprising:
blending the mixture to obtain a homogeneous blend of said oral medicine; wherein said acidic polysaccharide is in an amount of 0.1 to 20 parts by weight with respect to 1 part by weight of the basic medicine; and
forming the mixture comprising the homogeneous blend into granules, fine granules or a tablet for oral administration, wherein said basic medicine and acidic polysaccharide are in intimate contact in order to form an electric interaction and to prevent the basic medicine from dissolving in saliva; wherein said homogeneous blend further comprises a filler, a disintegrant, or both a filler and a disintegrant to obtain said homogeneous blend; wherein said acidic polysaccharide is at least one member selected from the group consisting of chondroitin sulfate, dextran sulfate, and salts thereof; and wherein said basic medicine is donepezil hydrochloride.

* * * * *